(12) United States Patent
Almutairi

(10) Patent No.: US 9,539,076 B2
(45) Date of Patent: Jan. 10, 2017

(54) APPARATUS AND SYSTEM FOR OXIDATIVE THERAPY IN DENTISTRY

(71) Applicant: Abdulrahman Almutairi, Woodside, NY (US)

(72) Inventor: Abdulrahman Almutairi, Woodside, NY (US)

( * ) Notice: Subject to any disclaimer, the term of this patent is extended or adjusted under 35 U.S.C. 154(b) by 194 days.

(21) Appl. No.: 14/522,896

(22) Filed: Oct. 24, 2014

(65) Prior Publication Data

US 2016/0113747 A1   Apr. 28, 2016

(51) Int. Cl.
*A61C 17/02* (2006.01)
*A61C 19/06* (2006.01)

(52) U.S. Cl.
CPC ......... *A61C 19/066* (2013.01); *A61C 17/0211* (2013.01); *A61C 19/063* (2013.01)

(58) Field of Classification Search
CPC ... A61C 17/00; A61C 17/0211; A61C 19/066; A61C 19/063
USPC .............. 433/27, 80; 601/164; 128/861–862
See application file for complete search history.

(56) References Cited

U.S. PATENT DOCUMENTS

| | | | |
|---|---|---|---|
| 3,731,675 A | 5/1973 | Kelly | |
| 4,164,940 A | 8/1979 | Quinby | |
| 5,293,880 A * | 3/1994 | Levitt | A63B 71/085 128/861 |
| 7,802,989 B2 | 9/2010 | Schemmer | |
| 8,617,090 B2 | 12/2013 | Fougere et al. | |
| 2008/0255498 A1 | 10/2008 | Houle | |
| 2012/0021375 A1 | 1/2012 | Binner et al. | |

FOREIGN PATENT DOCUMENTS

| | | |
|---|---|---|
| WO | WO 2009/027845 A2 | 3/2009 |
| WO | WO 2009/027845 A3 | 3/2009 |
| WO | WO 2013/039906 A1 | 3/2013 |

* cited by examiner

*Primary Examiner* — Carl H Layno
*Assistant Examiner* — Jon Eric C Morales
(74) *Attorney, Agent, or Firm* — Oblon, McClelland, Maier & Neustadt, L.L.P.

(57) ABSTRACT

An apparatus and a system for delivering a two-tier oxidative therapy to a dental patient. The apparatus is a mouthpiece made of rubber or thermoplastic elastomer that provides a full or partial coverage of the teeth and gums to be treated, firstly with vaporized hydrogen peroxide and later, ozone gas. The design of the mouthpiece encompassing multiple injection tubes also allows all surfaces of all teeth and gums to be treated at the same time, thereby offering a quick, painless and economical procedure to the dental patient.

15 Claims, 5 Drawing Sheets

APPARATUS AND SYSTEM FOR OXIDATIVE THERAPY IN DENTISTRY

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

FIELD OF THE DISCLOSURE

The present invention relates to an apparatus and a system for dental care. More specifically, the present relates to a mouthpiece equipped with and connected to an irrigation system for supply and dispensation of oxidizing gases.

BACKGROUND OF THE INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

No matter how diligently a person takes care of his or her dental health at home, harmful bacteria growing in the mouth may be removed only by a dental professional. Bacterial infections of gums and teeth lead to a variety of conditions and diseases such as dental plaque, tartar, cavities, gingivitis, tooth decay and periodontitis. Therefore, professional dental care is essential. For example, it is recommended that a person visits a dental professional every six months for at least a checkup and prophylactic teeth cleaning. However, visits to a dental professional are usually less than pleasant. Most visits can even be worrisome, fearful and painful experiences because of procedures like drilling, filling, removal or amputation and reconstruction.

Over the last decade, ozone therapy has been an emerging alternative, atraumatic therapeutic modality in medicine and dentistry. Ozone, which is a tri-atomic oxygen particle ($O_3$), is negatively charged and a natural oxidizing agent. Bad cells in our bodies such as bacteria, viruses and cancer cells typically carry positive charges and no anti-oxidants on their cell membranes, therefore attracting ozone particles that will perforate them and destroy them. In dentistry, a burst of liquefied ozone (ozonated water) or ozone gas is delivered to the teeth and gums in a treatment procedure that usually lasts no longer than 30 minutes.

Ozone can be used to help treat periodontal diseases by using ozonated water flushed below the gum line and or/or ozone gas infiltrated into the gum tissues and supporting tissues. Ozone is also used in both liquefied and gaseous forms during root canal treatment to kill bacteria, sterilize the canal system and to stimulate healing. As a gas, ozone can get to places on the oral cavity that liquids cannot access. This is because gas can permeate the tiny tubules that cannot otherwise be accessed, thereby providing a truly sterile, bacteria-free root canal system before sealing the canals.

Ozone can also be used to kill decay-causing bacteria. Since ozone is a gas, it can permeate into areas below the gum line, into the grooves of teeth and over the smooth surfaces of the teeth and will kill bacteria upon contact. If the decayed area or cavity is not too deep, then no restoration may be needed at all. If the area of decay is deeply cavitated and the bacteria is killed, then filling can be placed often times with no need for numbing. As ozone acts to recalcify tooth structure, areas of the tooth that have been treated with ozone are stronger than what was there before.

Additionally, for the same reason that ozone can harden compromised tooth structure, flooding a sensitive area or tooth with ozone gas can effectively eliminate sensitivity issues.

In contrast with traditional anti-bacterial treatments such as antibiotics and disinfectants, ozone therapy is relatively economical. Ozone is created by simply passing medical-grade pure oxygen through a corona discharge or ultraviolet generator.

Contraindications to ozone therapy are few and they include pregnancy, hyperthyroidism, severe anemia, severe myasthenia and active hemorrhage. Ozone allergy is very rare as it is high improbable that a person should be allergic to oxygen.

Yet, there exist some concerns about the safety of ozone therapy, especially inhalation of ozone and subsequently, blood ozonation. It is well established that due to its strong oxidizing properties, ozone, when inhaled, reacts with compounds in tissue linings of the lungs and triggers a cascade of pathological effects.

Accordingly, a need remains for devices, apparatuses and systems that provide ozone therapy to dental patients that is not only minimally invasive, but also has parameters such as therapeutic concentrations of ozone and modes of administration that are safe and well-defined.

SUMMARY

According to a first aspect, the present invention provides a mouthpiece for dental procedures. The mouthpiece comprises a U-shaped channel defined by a facial wall, a lingual wall and an occlusal wall to enclose a plurality of teeth on a jaw and gums proximal to the teeth. The mouthpiece includes a plurality of injection tubes in or on at least one of the facial wall, the lingual wall and the occlusal to deliver at least one treatment fluid into the channel and a suction tube connected to a facial surface of the mouthpiece and passing through the facial wall to deliver air into or out of the channel and the treatment fluid out of the channel.

In one or more embodiments, the injection tubes are disposed on the facial wall, the lingual wall and the occlusal wall.

In one or more alternative embodiments, the injection tubes are integral with the facial wall, the lingual wall and the occlusal wall to form flow channels under the surface of the walls.

In one or more embodiments, the mouthpiece is constructed of material selected from the group consisting of natural rubber, synthetic rubber, thermoplastic elastomer and combinations thereof.

In one or more embodiments, the injection tubes further include a plurality of holes.

In one or more embodiments, the injection tubes are constructed of a porous polymeric material selected from the group consisting of ultra-high molecular weight polyethylene (UHMWPE), high-density polyethylene (HDPE), propylene (PP), polytetrafluoroethylene (PTFE), polyvinylidene fluoride (PVDF), ethylene vinyl acetate (EVA), polyethersulfone (PES), polyurethane (PU), polyethylene/polypropylene (PE/PP) co-polymer and combinations thereof.

According to a second aspect, the present invention provides a dental system. The dental system comprises at least one mouthpiece according to the first aspect of the invention worn inside a patient's mouth, optionally a vaporized hydrogen peroxide source connected to the mouthpiece, an ozone gas source connected to the mouthpiece, a vacuum source connected to the mouthpiece and a gas meter connected to the vacuum source, the hydrogen peroxide source and the ozone source. The hydrogen peroxide source is configured to dispense an amount of vaporized hydrogen peroxide into the channel. The ozone source is configured to dispense an amount of ozone gas into the channel. The vacuum source is configured to remove air, the vaporized hydrogen peroxide and the ozone gas from the channel. The gas meter is configured to measure the amount of the air, vaporized hydrogen peroxide and ozone gas removed by the vacuum source.

In one or more embodiments, the ozone source is configured to dispense an amount of ozone gas into the channel when the amount of the vaporized hydrogen peroxide dispensed by the hydrogen peroxide source and the amount of the vaporized hydrogen peroxide removed by the vacuum source are less than a predetermined maximum disparity threshold.

In one or more embodiments, the dental system further comprises a computer system that is configured to operatively control the vacuum source, the hydrogen peroxide source, the ozone source and the gas meter.

In one or more embodiments, the dental system is configured to perform dental procedures selected from the group consisting of biofilm purging, periodontal pocket disinfection and osseous disinfection, prevention of dental caries, endodontic treatment, tooth extraction, tooth sensitivity, temporomandibular joint treatment, gum recession, root canal treatment, pain control, infection control, accelerated healing, tissue regeneration, controlling bad breath, remineralization of tooth surface, teeth whitening and combinations thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
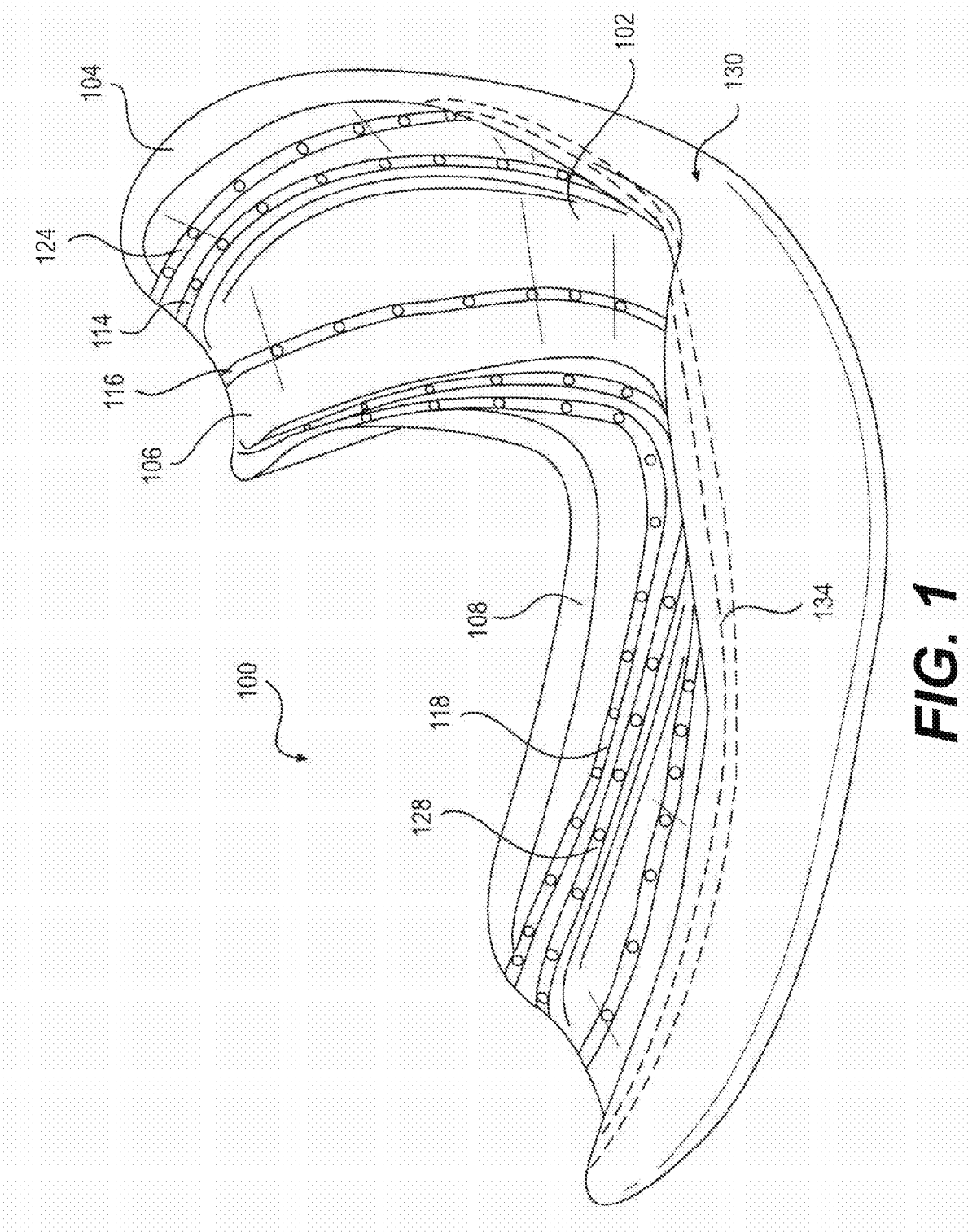
FIG. 1 illustrates a mouthpiece with a plurality of injection tubes and a suction tube according to one embodiment.

Referring now to the drawings, wherein like reference numerals designate identical or corresponding parts throughout the several views.

The present invention pertains to an apparatus and a system for multiple types of dental procedures that utilize two oxidizing gases, namely hydrogen peroxide and ozone, as sterilizing agents or disinfectants, healing stimulants, teeth whitening agents and enamel strengthening agents. Examples of dental treatment modalities of ozone therapy according to the present invention include, but are not limited to, biofilm purging (elimination of bacterial pathogens), periodontal pocket disinfection and osseous disinfection, prevention of dental caries, endodontic treatment, tooth extraction, tooth sensitivity, temporomandibular joint treatment, gum recession (exposed root surfaces), root canal treatment, pain control, infection control, accelerated healing, tissue regeneration, controlling halitosis (bad breath), remineralization of tooth surface and teeth whitening (bleaching).

Ozone may be dispensed in a liquefied (ozonated water) or a gaseous form. For purposes of the present invention, ozone gas is preferred because of its better permeability, which is especially crucial for places in the oral cavity that are very difficult and even impossible for liquids to access (e.g. root canal). Ozone generators such as corona discharge generators and ultraviolet generators produce ozone in both form medical-grade oxygen. Concentrations of ozone gas generated for dental procedures described herein are up to 50 $g/m^3$, for example, 20-50 $g/m^3$, preferably 25-40 $g/m^3$, more preferably 30-40 $g/m^3$.

Vaporized hydrogen peroxide is produced from a solution of liquid hydrogen peroxide ($H_2O_2$) and water, by generators or vaporizers specifically designed for the purposes. These hydrogen peroxide vaporizers initially dehumidify the ambient air, then produce the vapor by passing aqueous hydrogen peroxide over a vaporizer, and circulate the vapor at a programmed concentration of 140 ppm to 1400 ppm, depending on the infectious agent to be cleared. For purposes of the present invention, hydrogen peroxide vapor of concentrations 150-300 ppm, preferably 200-250 ppm, are used.

The apparatus for ozone dental procedures, as shown in FIG. 1, is a mouthpiece 100 with that may be mounted onto the upper jaw or the lower jaw of a dental patient, providing a full coverage of all or some of the teeth on the jaw and the gums proximal to the teeth. Mouthpiece 100 is made of natural rubber, synthetic rubber or thermoplastic elastomers and is therefore flexible. Thermoplastic elastomers (TPE), sometimes referred to as thermoplastic rubbers, are a class of synthetic copolymers or a physical mix of polymers (usually a plastic and a rubber) with both thermoplastic and elastomeric properties. Examples of commercial TPEs that may be used to make mouthpiece 100 include styrenic block copolymers (TPE-s), polyolefin blends (TPE-o), elastomeric alloys (TPE-v), thermoplastic polyurethanes (TPU), thermoplastic copolyester and thermoplastic polyamides (TPE-a), silicone elastomers, latex materials, styrene-butadiene rubber, SEBS rubber or any other TPEs known in the art and combinations thereof.

The mouthpiece 100 may also be available in different sizes, for example, adult size and child size. The mouthpiece 100 is flexible and may be bent or molded into a general U-shape to be inserted into a patient's mouth.

As seen in FIG. 1, the mouthpiece 100 includes a U-shaped or arc-shaped mouthpiece channel 102 that is defined by facial wall 104, occlusal wall 106 and lingual wall 108.

The mouthpiece channel 102 can further include one or more injection tubes. In one or more embodiments, the includes three tooth injection tubes, each having an internal diameter of 0.5-2.0 mm: tooth injection tube 114 on the facial wall 104, tooth injection tube 118 on the lingual wall 108 and tooth injection tube 116 on the occlusal wall 106. In one or more alternative embodiments, the tooth injection tubes 114, 116, 118 can be integral with the facial wall 104, occlusal wall 116 and lingual wall 108, respectively, thus forming flow channels under the surface of the walls.

Figure 2:
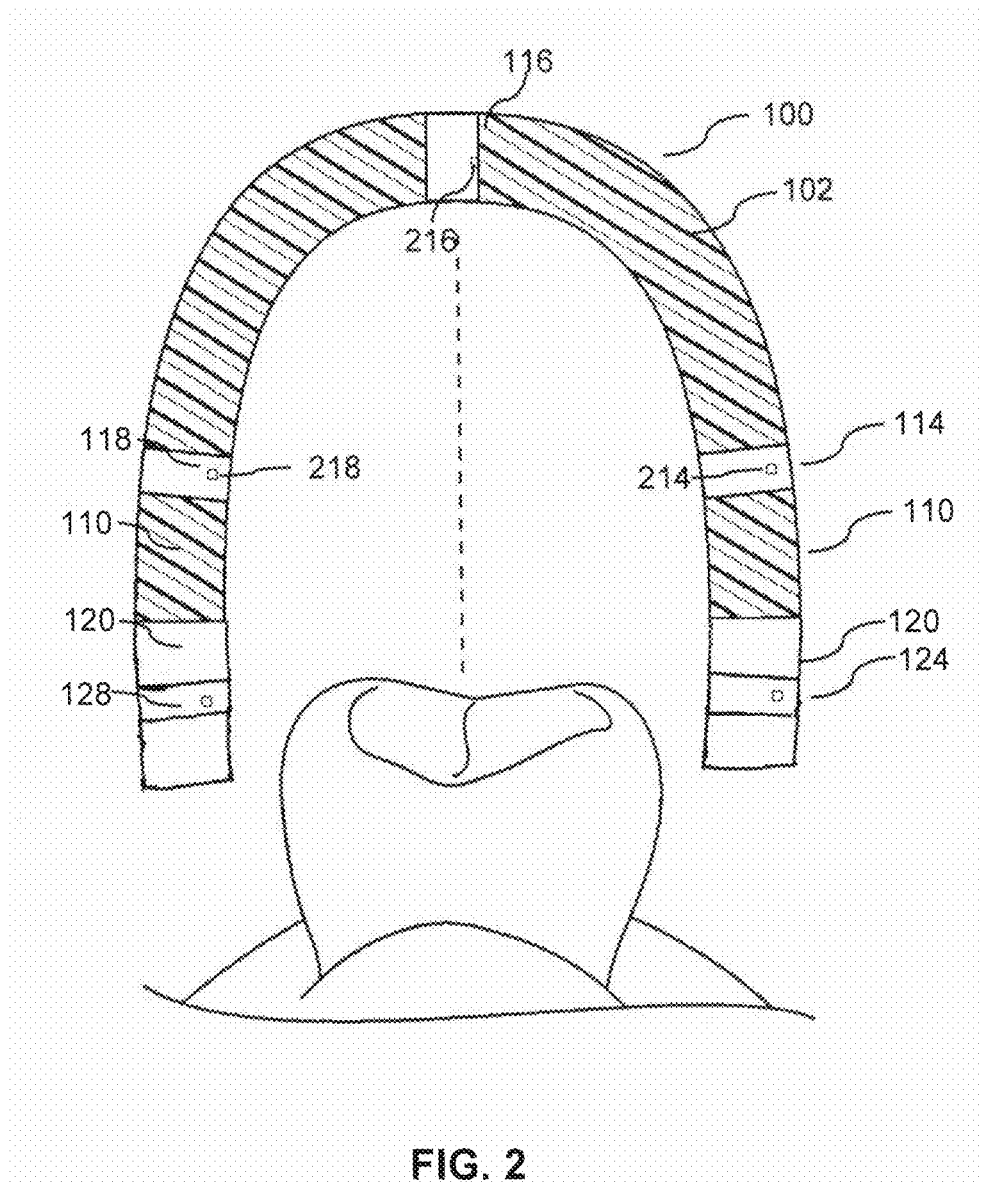
FIG. 2 provides an exploded view of a tooth receiving treatment fluids on the facial, lingual and occlusal surfaces of the tooth.

The three tooth injection tubes 114, 116, 118 can each include a plurality of holes along the length of tube, with each hole designed to inject dental treatment fluids. In one or more embodiments, there are a total of 16 holes on each tooth injection tube, one hole for each tooth. Therefore, each tooth on the upper or lower jaw receives treatment fluids (gas or liquid) directly from three holes that enable the facial (outside), lingual (inside) and occlusal (chewing) surfaces to be simultaneously treated. Each hole may have a diameter of 0.1-0.5 mm and the holes may be separated by 5-8 mm spacings between them. FIG. 2 provides an exploded view of how each tooth may be treated with treatment fluids coming from three directions from three holes 214, 216 and 218 (on tooth injection tubes 114, 116 and 118, respectively.

In an alternative embodiment, the tooth injection tubes 114, 116, 118 may be made of porous polymeric materials to allow dispensation of dental treatment fluids. Examples of porous polymeric materials include, for example, ultra-high molecular weight polyethylene (UHMWPE), high-density polyethylene (HDPE), propylene (PP), polytetrafluoroethylene (PTFE), polyvinylidene fluoride (PVDF), ethylene vinyl acetate (EVA), polyethersulfone (PES), polyurethane (PU) and polyethylene/polypropylene (PE/PP) co-polymer. These porous polymers have a gas permeability of at least $10^9$ cm$^2$/(sec·atm), for example $10^9$-$10^{11}$ cm$^2$/(sec·atm), at ambient temperature.

The facial wall 104, occlusal wall 106 and lingual wall 108 are not in contact with teeth so that the tooth injection tubes 114, 116, 118 are not constricted.

As used herein, dental treatment fluids encompass any fluid in liquid or gas form (including vapor) containing at least one active ingredient such as ozone, hydrogen peroxide, fluoride, carbamide peroxide and ammonium chloride. The dental treatment fluids may also further contain buffering agents, organic solvents (e.g. alcohols, aldehydes), water and other inactive ingredients.

Referring again to FIG. 1, the channel 102 can comprise one or more gum injection tubes. In one or more embodiments, the channel 102 includes two gum injection tubes: gum injection tube 124 facing the outside surface of the gums and gum injection tube 128 facing the inside surface of the gums. Gum injection tubes 124 and 128 each include a plurality of holes of 0.1-0.5 mm in diameter for dispensation of fluids to treat the front and back surfaces of the gums, respectively.

In addition, a suction tube 134 may be connected to a facial surface 130 of the mouthpiece 100. The suction tube 134 may pass through the facial wall 104 to deliver air into or out of the mouthpiece channel 102 and the treatment fluid out of the mouthpiece channel.

The mouthpiece 100 can also include a connection point for each of the tooth injection tubes 114, 116, 118, gum injection tubes 124, 128 and suction tube 134, for example, on the facial surface 130 (not shown).

Figure 3:
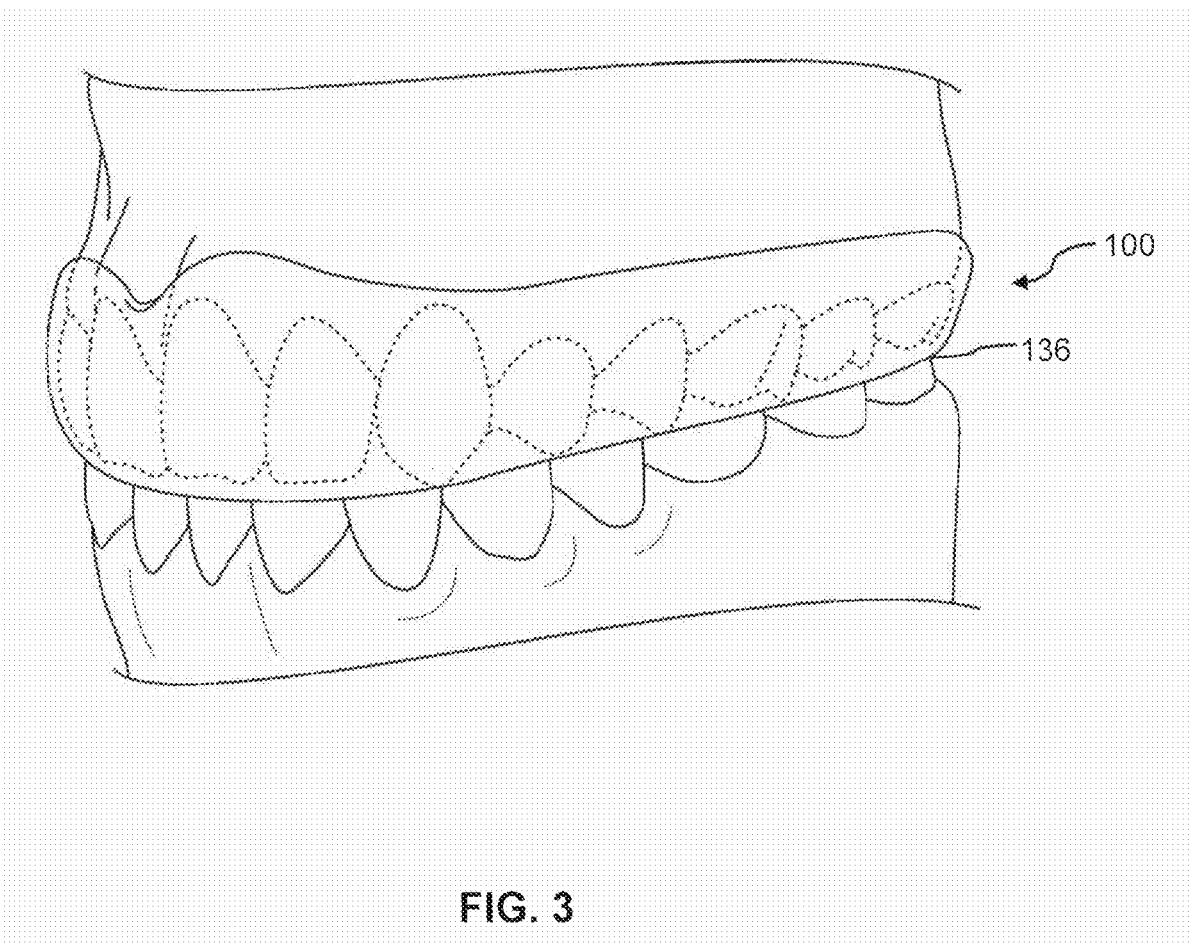
FIG. 3 illustrates the mouthpiece of FIG. 1 worn in a patient's mouth.

FIG. 3 shows the mouthpiece 100 being worn inside a patient's mouth. For clarity, the network of tooth and gum injection tubes in and the suction tube are not shown in FIG. 3. To secure mouthpiece 100 onto an upper jaw or a lower jaw of a patient, whichever desired, the mouthpiece 100 is placed on a jaw so that the mouthpiece channel 102 provides a full or partial coverage of the teeth on the jaw and the gums proximal to the teeth. Then, air is suctioned out of the channel 102 via suction tube 134. The vacuum generated by the suction results in channel 102 adhering firmly to the gums, sealing gaps between the back of the jaw and the edges of the mouthpiece and therefore providing a sealed coverage of the teeth and gums. The suction also results in the creation of lumen 136 around the teeth (see FIG. 3). After a dental procedure has been completed, the suction tube 134 delivers air or liquid to remove the vacuum in the mouthpiece channel 102 and release the mouthpiece 100. The vacuum pressure is maintained at no higher than 200 mmHg so as to cause minimal discomfort to the patient. Yet, the vacuum pressure generated is sufficient enough to cause the mouthpiece channel 102 to adhere firmly to the gums proximal to the teeth.

Figure 4:
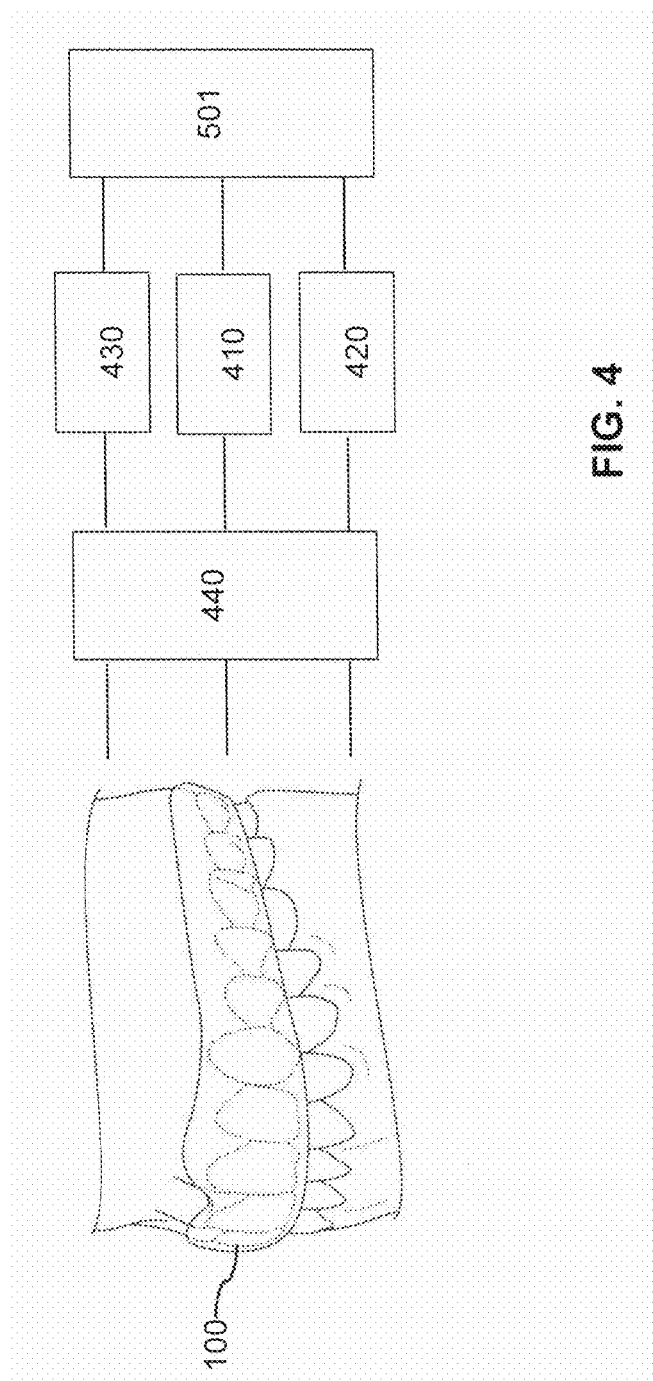
FIG. 4 illustrates a dental system according to one embodiment, wherein the mouthpiece of FIG. 1 is connected to a vacuum source, a gas meter, an ozone source, a hydrogen peroxide source and a computer system.

In FIG. 4, an exemplary embodiment of an ozone dental system according to the present invention is shown. The ozone dental system 400 includes at least one mouthpiece 100. In certain embodiments, two mouthpieces may be used to treat the complete set of teeth on both the upper jaw and the lower. All injection tubes and suction tubes of the mouthpieces of the ozone dental system 400 may be connected to an ozone source 410 (e.g. an ozone generator) and/or a hydrogen peroxide ($H_2O_2$) source 420 (e.g. a hydrogen peroxide vaporizer) via a plurality of tubings made of natural or synthetic rubber or thermoplastic elastomer materials and a plurality of connection points on the mouthpiece 100. The suction tube 134 of the mouthpieces, as described above, may be connected to a vacuum source 430 via a suction hose. The vacuum source 430 may be a simple vacuum pump or a vacuum system. The ozone source 410, the hydrogen peroxide source 420 and the vacuum source 430 may be connected to and coordinated by a computer system 501. The ozone dental system 400 may further include a gas meter 440 that is connected to the ozone source 410, the hydrogen peroxide source 420, the vacuum source 430 and the computer system 501. The gas meter 440 is a gas volume measuring device with examples including a eudiometer, vitalograph, water-displacement spirometer, pneumotachograph, rotameter, vane meter, Wright's spirometer, hot wire anemometer, ultrasonic flowmeter and mechanical flow transducer.

After the application of the mouthpiece 100 into a patient's mouth as described above, the volume or the amount of the air removed by the suction tubes is measured by the gas meter 440 and recorded in the computer system 501. In one embodiment, the hydrogen peroxide source 420 is then configured to dispense an amount of vaporized hydrogen peroxide (same amount as the removed air) through the tooth and gum injection tubes to flush the teeth and gums covered by the mouthpieces. The pressure gradient between the hydrogen peroxide source 420 and the vacuum also helps the transportation of the vapor. The lumen 136 serves as a container for carrying the dispensed vaporized hydrogen peroxide.

After the hydrogen peroxide treatment, the vaporized hydrogen peroxide is suctioned out via the suction tube 134 (not shown in FIG. 4) and the volume of the vapor is measured by the gas meter 440. The computer system 501 compares the suctioned volume to the volume of the vaporized hydrogen peroxide that has been earlier dispensed. The two values should be very similar. The difference in the values should be no greater than 5% based on the amount of the vaporized hydrogen peroxide dispensed, preferably no greater than 2%, even more preferably no greater than 1%. A suctioned volume that is a lot smaller than the dispensed volume is indicative of leakage and that the mouthpieces have not been properly applied. A leakage not only significantly reduces the effectiveness of the treatment but also increases the risk of ozone inhalation by the patient. The computer system 501 may be configured to detect a maximum disparity threshold between the suctioned volume and the dispensed volume of the vaporized hydrogen peroxide.

If no leakage is detected or a leakage has been resolved by re-application of the mouthpieces, the dental procedure resumes and the ozone source 410 is configured dispense ozone (preferably ozone gas) to treat the teeth and gums. After the treatment, the ozone is removed via the suction tube. The vacuum is removed by the vacuum source 430 pumping air into the mouthpiece channel 102 via the suction tube 134 and the mouthpiece(s) 100 may be released. The mouthpiece(s) can then be safely removed from the patient's mouth. All air and treatment fluids (e.g. vaporized hydrogen peroxide and ozone gas) removed by the vacuum source 430 are treated as biohazard wastes as they potentially carry microorganisms and are therefore disposed in compliance with biohazard procedures.

Therefore, vaporized hydrogen peroxide is used not only as a dental treatment fluid but also as a safety measure to ensure that there is no leakage before ozone is applied. Hydrogen peroxide, like ozone, is has sterilizing properties and is inexpensive. Hydrogen peroxide is routinely used in medicine and dentistry as a sterilizer.

As the design of the mouthpieces enables each tooth to be simultaneously treated by vaporized hydrogen peroxide and later ozone, the entire treatment process may be completed in as little as five minutes or less. On the contrary, in a dental system wherein a handpiece is designed to ozone-treat one tooth at a time, it takes a significantly longer period to treat a patient's complete set of teeth (i.e. approximately 22 minutes and 14 minutes for an adult patient and a child patient, respectively, with approximately 40 seconds spent on each tooth).

In one embodiment, the ozone dental system 400 may further include a container wherein all air, vaporized hydrogen peroxide and ozone gas removed via the suction tube and measured by the gas meter may be safely disposed.

Figure 5:
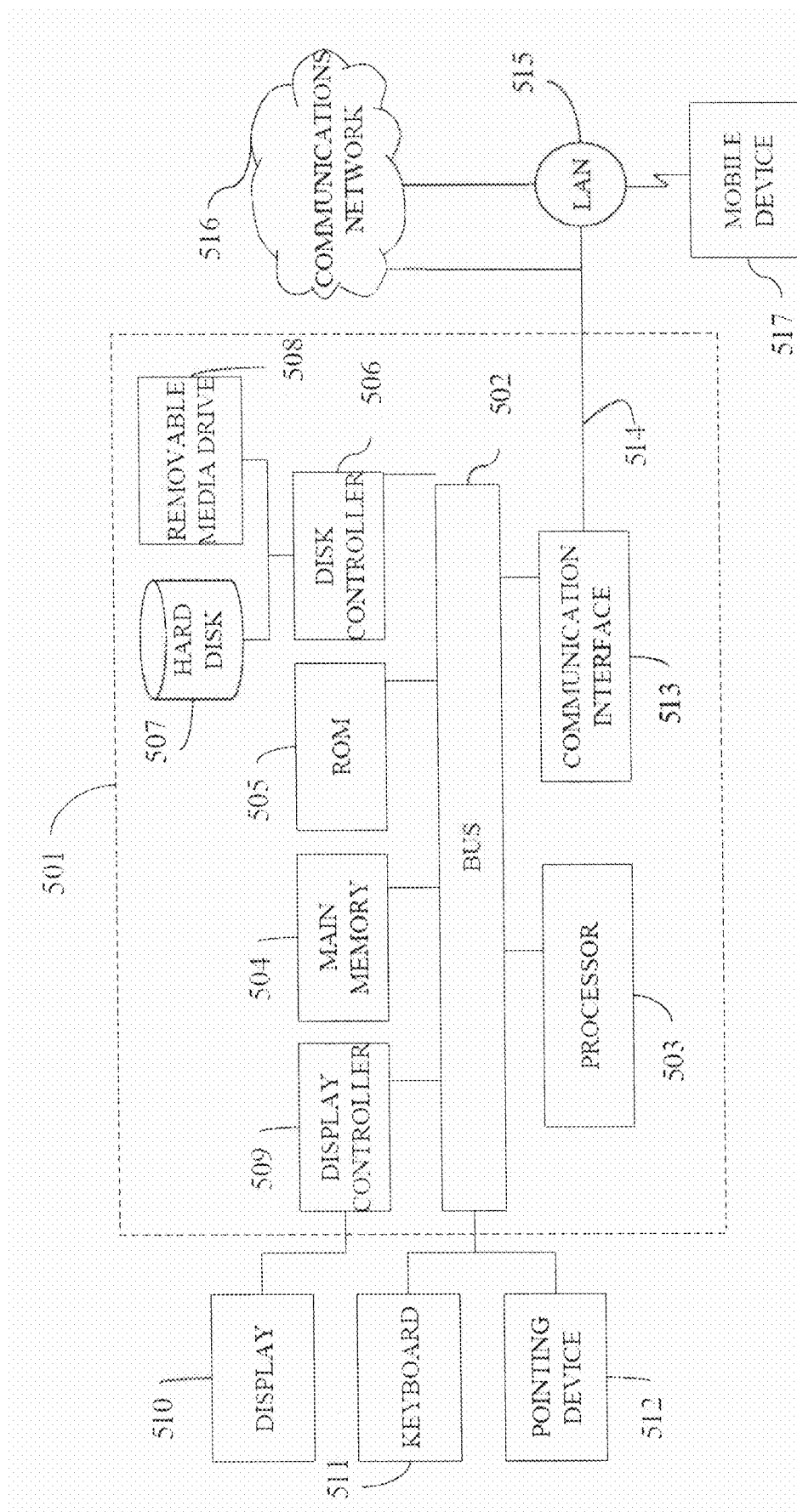
FIG. 5 is a block diagram of the hardware components of the computer system of FIG. 4.

FIG. 5 illustrates the hardware components of a computer system 501 upon which an embodiment of the present invention may be implemented. The computer system 501 includes a bus 502 or other communication mechanism for communicating information, and a processor 503 coupled with the bus 502 for processing the information. The computer system 501 also includes a main memory 504, such as a random access memory (RAM) or other dynamic storage device (e.g., dynamic RAM (DRAM), static RAM (SRAM), and synchronous DRAM (SDRAM)), coupled to the bus 502 for storing information and instructions to be executed by processor 503. In addition, the main memory 504 may be used for storing temporary variables or other intermediate information during the execution of instructions by the processor 503. The computer system 501 further includes a read only memory (ROM) 505 or other static storage device (e.g., programmable ROM (PROM), erasable PROM (EPROM), and electrically erasable PROM (EEPROM)) coupled to the bus 502 for storing static information and instructions for the processor 503.

The computer system 501 also includes a disk controller 506 coupled to the bus 502 to control one or more storage devices for storing information and instructions, such as a magnetic hard disk 507, and a removable media drive 508 (e.g., floppy disk drive, read-only compact disc drive, read/write compact disc drive, compact disc jukebox, tape drive, and removable magneto-optical drive). The storage devices may be added to the computer system 501 using an appropriate device interface (e.g., small computer system interface (SCSI), integrated device electronics (IDE), enhanced-IDE (E-IDE), direct memory access (DMA), or ultra-DMA).

The computer system 501 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs).

The computer system 501 may also include a display controller 509 coupled to the bus 502 to control a display 510, such as a cathode ray tube (CRT), for displaying information to a computer user. The computer system includes additional input devices aside from the gas meter, the vacuum source, the hydrogen peroxide source and the ozone source (not shown in FIG. 5). These additional input devices may include a keyboard 511 and a pointing device 512, for interacting with a computer user and providing information to the processor 503. The pointing device 512, for example, may be a mouse, a trackball, or a pointing stick for communicating direction information and command selections to the processor 503 and for controlling cursor movement on the display 510. In addition, a printer may provide printed listings of data stored and/or generated by the computer system 501.

The computer system 501 performs a portion or all of the processing steps of the invention in response to the processor 503 executing one or more sequences of one or more instructions contained in a memory, such as the main memory 504. Such instructions may be read into the main memory 504 from another computer readable medium, such as a hard disk 507 or a removable media drive 5208. One or more processors in a multi-processing arrangement may also be employed to execute the sequences of instructions contained in main memory 504. In alternative embodiments, hard-wired circuitry may be used in place of or in combination with software instructions. Thus, embodiments are not limited to any specific combination of hardware circuitry and software.

As stated above, the computer system 501 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 501, for driving a device or devices for implementing the invention, and for enabling the computer system 501 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 503 for execution. A computer readable medium may take many forms, including but not limited to, non-volatile media, volatile media, and transmission media. Non-volatile media includes, for example, optical, magnetic disks, and magneto-optical disks, such as the hard disk 507 or the removable media drive 508. Volatile media includes dynamic memory, such as the main memory 504. Transmission media includes coaxial cables, copper wire and fiber optics, including the wires that make up the bus 502. Transmission media also may also take the form of acoustic or light waves, such as those generated during radio wave and infrared data communications.

Various forms of computer readable media may be involved in carrying out one or more sequences of one or more instructions to processor 503 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 501 may receive the data on the telephone line and use an infrared transmitter to convert the data to an infrared signal. An infrared detector coupled to the bus 502 can receive the data carried in the infrared signal and place the data on the bus 502. The bus 502 carries the data to the main memory 504, from which the processor 503 retrieves and executes the instructions. The instructions received by the main memory 504 may optionally be stored on storage device 507 or 508 either before or after execution by processor 503.

The computer system 501 also includes a communication interface 513 coupled to the bus 502. The communication interface 513 provides a two-way data communication coupling to a network link 514 that is connected to, for example, a local area network (LAN) 515, or to another communications network 516 such as the Internet. For example, the communication interface 513 may be a network interface card to attach to any packet switched LAN. As another example, the communication interface 513 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 513 sends and receives electrical, electromagnetic or optical signals that carry digital data streams representing various types of information.

The network link 514 typically provides data communication through one or more networks to other data devices. For example, the network link 514 may provide a connection to another computer through a local network 515 (e.g., a LAN) or through equipment operated by a service provider, which provides communication services through a communications network 516. The local network 514 and the communications network 516 use, for example, electrical, electromagnetic, or optical signals that carry digital data streams, and the associated physical layer (e.g., CAT 5 cable, coaxial cable, optical fiber, etc). The signals through the various networks and the signals on the network link 514 and through the communication interface 513, which carry the digital data to and from the computer system 501 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 501 can transmit and receive data, including program code, through the network(s) 515 and 516, the network link 514 and the communication interface 513. Moreover, the network link 514 may provide a connection through a LAN 515 to a mobile device 517 such as a personal digital assistant (PDA) laptop computer, or cellular telephone.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A mouthpiece for dental procedures, comprising:
 a U-shaped channel defined by a facial wall, a lingual wall and an occlusal wall to enclose a plurality of teeth on a jaw and gums proximal to the teeth;
 the mouthpiece having a plurality of injection tubes in or on at least one of the facial wall, the lingual wall and the occlusal wall to deliver at least one treatment fluid into the channel; and
 a suction tube connected to a facial surface of the mouthpiece and passing through the facial wall to deliver air into or out of the channel and the treatment fluid out of the channel;
 wherein the injection tubes are constructed of a porous polymeric material selected from the group consisting of ultra-high molecular weight polyethylene (UHMWPE), high-density polyethylene (HDPE), propylene (PP), polytetrafluoroethylene (PTFE), polyvinylidene fluoride (PVDF), ethylene vinyl acetate (EVA), polyethersulfone (PES), polyurethane (PU), polyethylene/polypropylene (PE/PP) co-polymer and combinations thereof.

2. The mouthpiece of claim 1, wherein the injection tubes are disposed on the facial wall, the lingual wall and the occlusal wall.

3. The mouthpiece of claim 1, wherein the injection tubes are integral with the facial wall, the lingual wall and the occlusal wall to form flow channels under the surface of the walls.

4. The mouthpiece of claim 1, wherein the mouthpiece is constructed of material selected from the group consisting of natural rubber, synthetic rubber, thermoplastic elastomer and combinations thereof.

5. The mouthpiece of claim 1, wherein the injection tubes further include a plurality of holes.

6. A dental system, comprising:
at least one mouthpiece having a U-shaped channel and worn inside a patient's mouth;
optionally a vaporized hydrogen peroxide source connected to the mouthpiece;
an ozone gas source connected to the mouthpiece;
a vacuum source connected to the mouthpiece; and
a gas meter connected to the vacuum source, the hydrogen peroxide source and the ozone source;
wherein the channel is defined by a facial wall, a lingual wall and an occlusal wall to enclose a plurality of teeth on a jaw gums proximal to the teeth;
wherein the mouthpiece includes a plurality of injection tubes in or on at least one of the facial wall, the lingual wall and the occlusal wall to deliver at least one treatment fluid into the channel;
wherein the hydrogen peroxide source is configured to dispense an amount of vaporized hydrogen peroxide into the channel;
wherein the ozone source is configured to dispense an amount of ozone gas into the channel;
wherein the vacuum source is configured to remove air, the vaporized hydrogen peroxide and the ozone gas from the channel; and
wherein the gas meter is configured to measure the amount of the air, vaporized hydrogen peroxide and ozone gas removed by the vacuum source.

7. The dental system of claim 6, wherein the mouthpiece further comprises a suction tube connected to a facial surface of the mouthpiece and passing through the facial wall to deliver air into or out of the channel and the treatment fluid out of the channel.

8. The dental system of claim 6, wherein the injection tubes are disposed on the facial wall, the lingual wall and the occlusal wall.

9. The dental system of claim 6, wherein the injection tubes are integral with the facial wall, the lingual wall and the occlusal wall to form flow channels under the surface of the walls.

10. The dental system of claim 6, wherein the mouthpiece is constructed of material selected from the group consisting of natural rubber, synthetic rubber, thermoplastic elastomer and combinations thereof.

11. The dental system of claim 6, wherein the injection tubes further include a plurality of holes.

12. The dental system of claim 6, wherein the injection tubes are constructed of a porous polymeric material selected from the group consisting of ultra-high molecular weight polyethylene (UHMWPE), high-density polyethylene (HDPE), propylene (PP), polytetrafluoroethylene (PTFE), polyvinylidene fluoride (PVDF), ethylene vinyl acetate (EVA), polyethersulfone (PES), polyurethane (PU), polyethylene/polypropylene (PE/PP) co-polymer and combinations thereof.

13. The dental system of claim 6, wherein the ozone source is configured to dispense an amount of ozone gas into the channel when the amount of the vaporized hydrogen peroxide dispensed by the hydrogen peroxide source and the amount of the vaporized hydrogen peroxide removed by the vacuum source are less than a predetermined maximum disparity threshold.

14. The dental system of claim 6, further comprising a computer system;
wherein the computer system is configured to operatively control the vacuum source, the hydrogen peroxide source, the ozone source and the gas meter.

15. The dental system of claim 6, wherein the dental system is configured to perform dental procedures selected from the group consisting of biofilm purging, periodontal pocket disinfection and osseous disinfection, prevention of dental caries, endodontic treatment, tooth extraction, tooth sensitivity, temporomandibular joint treatment, gum recession, root canal treatment, pain control, infection control, accelerated healing, tissue regeneration, controlling bad breath, remineralization of tooth surface, teeth whitening and combinations thereof.

* * * * *